US012699047B2

(12) United States Patent
Osherovich et al.

(10) Patent No.: US 12,699,047 B2
(45) Date of Patent: Aug. 4, 2026

(54) SYSTEM AND METHOD FOR DETECTING AND CONTROLLING A SPECTRUM OF A LIGHT SOURCE OF A HYPERSPECTRAL IMAGING SYSTEM

(71) Applicant: NEOLITHICS LTD, Kfar Sirkin (IL)

(72) Inventors: Eliyahu Osherovich, Haifa (IL); Timea Ignat, Midreshet Ben Gurion (IL); Ze'ev Schmilovitch, Yehud-Monosson (IL)

(73) Assignee: NEOLITHICS LTD., Kfar Sirkin (IL)

( * ) Notice: Subject to any disclaimer, the term of this patent is extended or adjusted under 35 U.S.C. 154(b) by 9 days.

(21) Appl. No.: 18/782,098

(22) Filed: Jul. 24, 2024

(65) Prior Publication Data

US 2026/0029335 A1 Jan. 29, 2026

(51) Int. Cl.
| | |
|---|---|
| *G01N 21/31* | (2006.01) |
| *G01J 3/28* | (2006.01) |
| *H05B 47/11* | (2020.01) |
| *H05B 47/28* | (2020.01) |
| *G01N 33/02* | (2006.01) |

(52) U.S. Cl.
CPC ............ *G01N 21/31* (2013.01); *G01J 3/2823* (2013.01); *H05B 47/11* (2020.01); *H05B 47/28* (2020.01); *G01N 33/025* (2013.01); *G01N 2201/127* (2013.01)

(58) Field of Classification Search
CPC ............ G01J 2003/2826; G01J 3/2823; G01N 33/025; G01N 21/31; H05B 47/28
See application file for complete search history.

(56) References Cited

U.S. PATENT DOCUMENTS

| | | | | |
|---|---|---|---|---|
| 5,903,584 | A | * 5/1999 | Jiahn-Chang | ........... H01S 5/023 372/36 |
| 7,520,634 | B2 | 4/2009 | Ducharme et al. | |
| 8,502,974 | B2 * | 8/2013 | Johnsen | ............... G01J 3/2823 348/148 |
| 2002/0165456 | A1 * | 11/2002 | Canpolat | ................ A61B 5/444 600/473 |
| 2019/0271591 | A1 | 9/2019 | Chen et al. | |
| 2023/0266234 | A1 | 8/2023 | Oeguen et al. | |

FOREIGN PATENT DOCUMENTS

| | | | | |
|---|---|---|---|---|
| CN | 204859711 U | * | 12/2015 | |
| CN | 110383049 A | * | 10/2019 | ............. B07C 5/342 |
| CN | 111855595 A | | 10/2020 | |
| DE | 102023111914 A1 | * | 11/2023 | ........... G01J 3/2803 |
| JP | 2006170669 A | * | 6/2006 | |
| KR | 20090109027 A | * | 10/2009 | |

(Continued)

OTHER PUBLICATIONS

Binaryupdates, "LDR with Arduino—Measure Light Intensity using Photoresistor", Oct. 16, 2019 (Year: 2019).*

(Continued)

*Primary Examiner* — Maurice C Smith
(74) *Attorney, Agent, or Firm* — The Roy Gross Law Firm, LLC; Roy D. Gross

(57) ABSTRACT

There is provided a system and method for determining external and/or internal attributes of an object using hyperspectral imaging, while taking into consideration changes in the spectral emission profile of the light source used for the imaging.

9 Claims, 6 Drawing Sheets

(56)  References Cited

FOREIGN PATENT DOCUMENTS

| KR | 20100016686 | A | * | 2/2010 |  |
| WO | WO-2008019479 | A1 | * | 2/2008 | ......... G03G 9/09741 |
| WO | 2023285538 | A1 |  | 1/2023 |  |

OTHER PUBLICATIONS

Florian Uhl, "Submerged Kelp Detection with Hyperspectral Data", 2016 (Year: 2016).*

Of Emiliano Cimoli, "An Under-Ice Hyperspectral and RGB Imaging System to Capture Fine-Scale Biophysical Properties of Sea Ice", Sep. 2019 (Year: 2019).*

Ito, K., Higashi, H., Hietanen, A., Fält, P., Hine, K., Hauta-Kasari, M., & Nakauchi, S. (2022). The Optimization of the Light-Source Spectrum Utilizing Neural Networks for Detecting Oral Lesions. Journal of Imaging, 9(1), 7. https://doi.org/10.3390/jimaging9010007.

Zhao, W., & Du, S. (2016). Spectral-spatial feature extraction for hyperspectral image classification: A dimension reduction and deep learning approach. IEEE Transactions on Geoscience and Remote Sensing, 54(8), 4544-4554. doi: 10.1109/TGRS.2016.2543748.

R. Paschotta, article on "Wavelength-tunable Light Sources" in the RP Photonics Encyclopedia, https://doi.org/10.61835/4dn, retrieved Jul. 22, 2024.

Davidson, M. W. (2021). Education in Microscopy and Digital Imaging. ZEISS. Available online: [https://zeiss-campus.magnet.fsu.edu/articles/lightsources/tungstenhalogen.html].

* cited by examiner

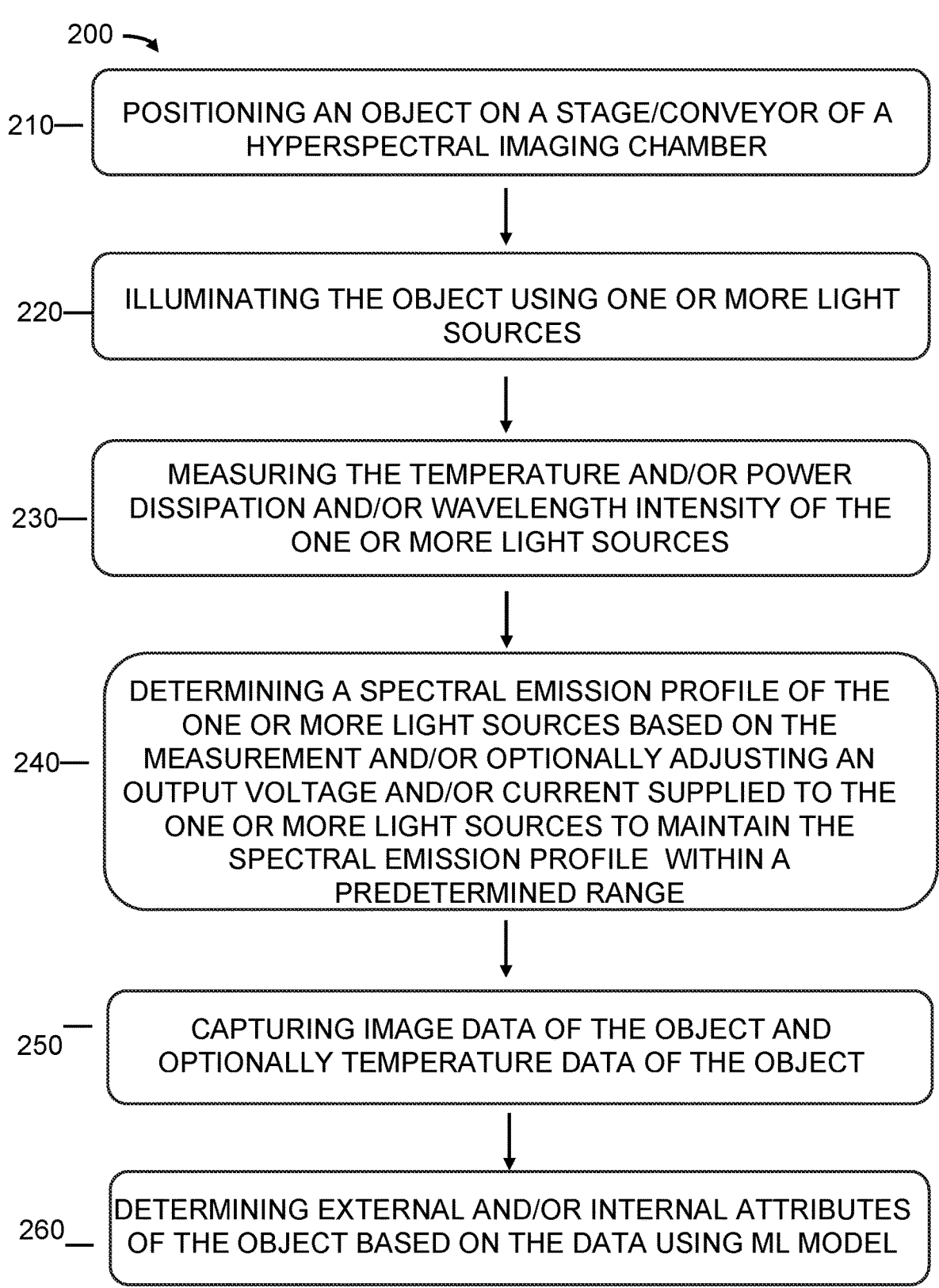

200

210— POSITIONING AN OBJECT ON A STAGE/CONVEYOR OF A HYPERSPECTRAL IMAGING CHAMBER

220— ILLUMINATING THE OBJECT USING ONE OR MORE LIGHT SOURCES

230— MEASURING THE TEMPERATURE AND/OR POWER DISSIPATION AND/OR WAVELENGTH INTENSITY OF THE ONE OR MORE LIGHT SOURCES

240— DETERMINING A SPECTRAL EMISSION PROFILE OF THE ONE OR MORE LIGHT SOURCES BASED ON THE MEASUREMENT AND/OR OPTIONALLY ADJUSTING AN OUTPUT VOLTAGE AND/OR CURRENT SUPPLIED TO THE ONE OR MORE LIGHT SOURCES TO MAINTAIN THE SPECTRAL EMISSION PROFILE WITHIN A PREDETERMINED RANGE

250 CAPTURING IMAGE DATA OF THE OBJECT AND OPTIONALLY TEMPERATURE DATA OF THE OBJECT

260— DETERMINING EXTERNAL AND/OR INTERNAL ATTRIBUTES OF THE OBJECT BASED ON THE DATA USING ML MODEL

FIG. 2

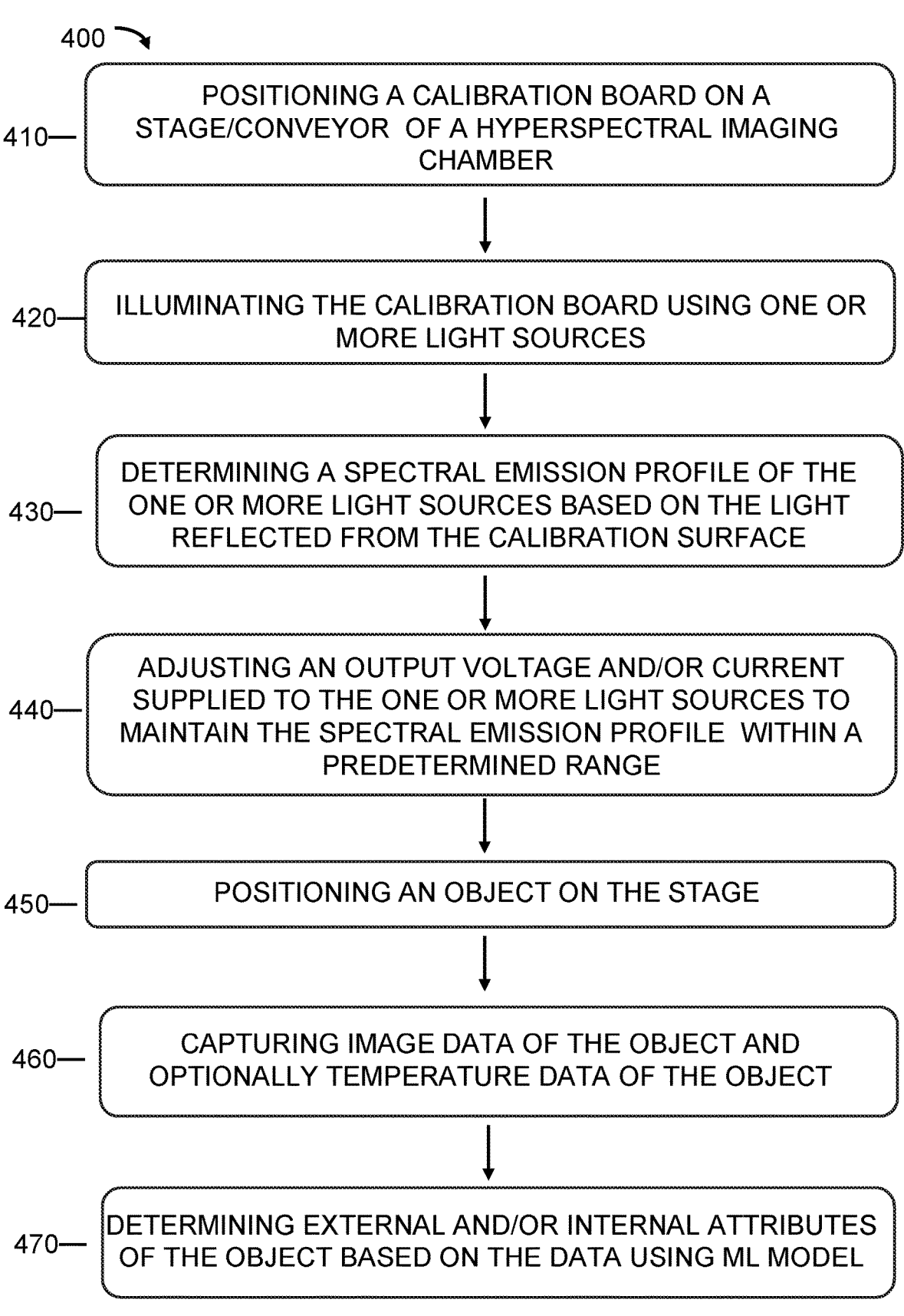

400

410— POSITIONING A CALIBRATION BOARD ON A STAGE/CONVEYOR OF A HYPERSPECTRAL IMAGING CHAMBER

420— ILLUMINATING THE CALIBRATION BOARD USING ONE OR MORE LIGHT SOURCES

430— DETERMINING A SPECTRAL EMISSION PROFILE OF THE ONE OR MORE LIGHT SOURCES BASED ON THE LIGHT REFLECTED FROM THE CALIBRATION SURFACE

440— ADJUSTING AN OUTPUT VOLTAGE AND/OR CURRENT SUPPLIED TO THE ONE OR MORE LIGHT SOURCES TO MAINTAIN THE SPECTRAL EMISSION PROFILE WITHIN A PREDETERMINED RANGE

450— POSITIONING AN OBJECT ON THE STAGE

460— CAPTURING IMAGE DATA OF THE OBJECT AND OPTIONALLY TEMPERATURE DATA OF THE OBJECT

470— DETERMINING EXTERNAL AND/OR INTERNAL ATTRIBUTES OF THE OBJECT BASED ON THE DATA USING ML MODEL

FIG. 4

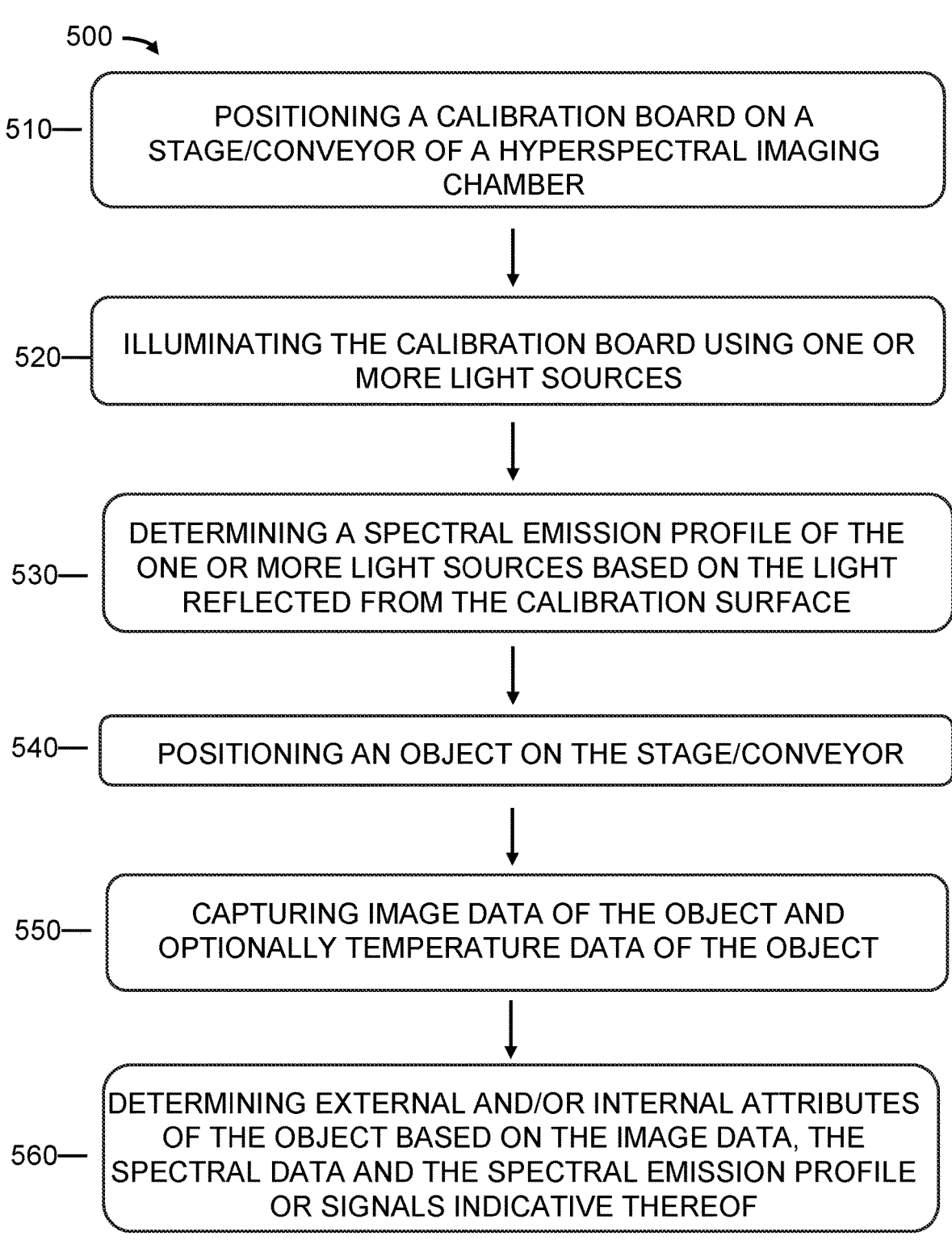

500

510— POSITIONING A CALIBRATION BOARD ON A STAGE/CONVEYOR OF A HYPERSPECTRAL IMAGING CHAMBER

520— ILLUMINATING THE CALIBRATION BOARD USING ONE OR MORE LIGHT SOURCES

530— DETERMINING A SPECTRAL EMISSION PROFILE OF THE ONE OR MORE LIGHT SOURCES BASED ON THE LIGHT REFLECTED FROM THE CALIBRATION SURFACE

540— POSITIONING AN OBJECT ON THE STAGE/CONVEYOR

550— CAPTURING IMAGE DATA OF THE OBJECT AND OPTIONALLY TEMPERATURE DATA OF THE OBJECT

560— DETERMINING EXTERNAL AND/OR INTERNAL ATTRIBUTES OF THE OBJECT BASED ON THE IMAGE DATA, THE SPECTRAL DATA AND THE SPECTRAL EMISSION PROFILE OR SIGNALS INDICATIVE THEREOF

FIG.
5

SYSTEM AND METHOD FOR DETECTING AND CONTROLLING A SPECTRUM OF A LIGHT SOURCE OF A HYPERSPECTRAL IMAGING SYSTEM

TECHNOLOGICAL FIELD

The present disclosure generally relates to a system and method for detecting, and optionally controlling a spectrum of a light source of a hyperspectral imaging system and/or for analysing hyperspectral images, in particular hyperspectral images of a crop, while taking into account the spectral emission profile of the light source.

BACKGROUND

Acceptance checkup/test of produce are conducted as routine procedures for fruits and vegetables.

Recently, imaging has been applied as an emerging scientific tool in non-destructive fruit and vegetable quality assessment. However, these imaging methods require that the light source illuminating the crop has an essentially constant spectral emission profile in order for the assessment to be reliable.

However, the spectral emission profile of light sources tends to change. For example, the spectral imaging profile of light sources such as tungsten-halogen lamp shifts towards shorter wavelengths as the temperature of the halogen lamp approaches the limiting melting point of tungsten, such that the proportion of visible wavelengths emitted by the halogen lamp increases substantially. Similarly, the spectral imaging profile of light sources change with use/time.

Accordingly, there is a need for a system and methods for hyperspectral non-destructive quality analysis of crops which takes into consideration the spectral imaging profile of the light source used to illuminate the crop.

SUMMARY OF THE INVENTION

There is provided herein a system and method for monitoring external and/or internal attributes of an object, in particular fruits and vegetables, which compensates for/takes into consideration changes in the spectral emission profile of the light source, used to illuminate the object.

According to some embodiments, this may be achieved by monitoring a temperature, and/or power dissipation and/or specific wavelength intensity followed by an adjustment (if required) of the voltage/current flow to the light source based thereon, prior to conducting the imaging of the object. Advantageously, this may ensure not only a more reliable image-based inspection of the object, but also increase the lifetime of the lamp.

According to another embodiment, the compensation for changes in the spectral emission profile of the light source may be achieved by monitoring a temperature and/or power dissipation and/or a specific wavelength intensity of the light source, as before, but instead of making changes to the output voltage and/or current supplied to the light source, using the monitored temperature, and/or power dissipation and/or wavelength intensity as an input to a machine learning model trained to determine the external and/or internal attributes of the object, based on hyperspectral imaging thereof. Advantageously, this may ensure a reliable image-based inspection of the object, even when the quality of the light source has deteriorated, and/or its spectral emission profile changed.

According to some embodiment, the compensation for changes in the spectral emission profile of the light source may in addition or alternatively include illuminating a calibration board which reflect light the spectrum and/or intensity of which has a known dependence on the actual spectral emission profile of the light source (as opposed to its theoretical spectral emission profile). The actual spectral emission profile of the light source may then be inputted into a machine learning model trained to determine the external and/or internal attributes of the object, based on hyperspectral imaging thereof. As before, this may advantageously ensure a reliable image-based inspection of the object even when the quality of the light source has deteriorated and its spectral emission profile changed.

According to some embodiments, there is provided a system for determining external and/or internal attributes of an object, the system including:

a light source configured to illuminate an object;

a light source sensor configured to measure a temperature of the light source and/or a power dissipation of the light source and/or an intensity of a specific wavelength of the light emitted by the light source;

a power supply configured to supply power to the light source;

a control unit configured to adjust a frequency, a current, and/or a voltage of the power supply, based on the measured temperature and/or power dissipation and/or the intensity of the specific wavelength of the light source, whereby the spectral emission profile of the light source is maintained within a predetermined range;

one or more optical sensors operating in visual and/or non-visual spectra and configured to capture images of the illuminated object; and a processing unit configured to receive spectral data from the one or more optical sensors and derive an internal and/or external quality attribute of the object based on the received spectral data.

According to some embodiments, the light source is a halogen light source, a xenon light source or a LED. Each possibility is a separate embodiment. According to some embodiments, the light source is a halogen light source.

According to some embodiments, the light source sensor is a temperature sensor, selected from a thermal sensor, a thermocouple, a laser sensor, a thermistor or any combination thereof. Each possibility is a separate embodiment.

According to some embodiments, the light source sensor is a diode receptor configured to measure the intensity of the specific wavelength of the light emitted by the light source.

According to some embodiments, the light source sensor is a current and/or voltage monitor, such as but not limited to an AVOmeter.

According to some embodiments, the system further includes one or more additional sensors configured to measure one or more parameters of the illuminated object. According to some embodiments, the additional sensor may be selected from a distance sensor, a lidar sensor, a depth sensor, a temperature sensor, an ultrasonic sensor, fluorescence sensor, X-ray sensor, XRF (X-ray fluorescence) sensor, MRI sensor, dielectric sensor, or any combination thereof. Each possibility is a separate embodiment.

According to some embodiments, the processing unit is configured to fuse the received spectral data with data received from additional sensors. According to some embodiments, the internal and/or external quality attributes of the produce comprises feeding the fused data into a machine learning model.

According to some embodiments, the one or more optical sensors comprise at least one hyperspectral camera. Additionally or alternatively, the one or more optical sensors comprise at least one RGB camera.

According to some embodiments, the processing unit is further configured to produce a report presenting the derived internal and/or external quality attributes.

According to some embodiments, the control unit is further configured to: set one or more opto-mechanical parameters of the one or more optical sensors. According to some embodiments, the opto-mechanical parameters selected from: a field of view of the one or more optical sensors, exposure time, aperture, gain, sensitivity, frame rate and any combination thereof; and/or to set a position, orientation, light projection and/or light intensity of the light source. Each possibility is a separate embodiment.

According to some embodiments, the one or more internal and/or external parameters are selected from chemical composition, biochemical composition, physical composition and biophysical composition, like dry matter, total soluble solids, sugar content, moisture, acidity, titratable acidity, pH, starch, ascorbic acid, external and/or internal defects, moldiness, decay, pigments, size, shape, texture, contaminants, and any combination thereof. Each possibility is a separate embodiment.

According to some embodiments, the processing unit is further configured to derive one or more complex parameters from the one or more of the internal and/or external quality attributes, wherein the one or more complex attribute comprise maturity, ripeness, shelf-life, storability and any combination thereof. Each possibility is a separate embodiment.

According to some embodiments, there is provided a system for determining external and/or internal attributes of an object, the system comprising:

a light source configured to illuminate the object;

a light source sensor configured to measure a temperature of the light source and/or a power dissipation of the light source and/or an intensity of a specific wavelength of the light emitted by the light source;

one or more optical sensors operating in visual and/or non-visual spectra and configured to capture images of the illuminated object; and a processing unit configured to:

receive as an input one or more signals from the light source sensor, the one or more signals indicative of a spectral emission profile of the light source;

receive spectral data from the one or more optical sensors; and derive an internal and/or external quality attribute of the object based on the received one or more signals indicative of a spectral emission profile of the light source and based on the received spectral data.

According to some embodiments, the light source is a halogen light source, a xenon light source or a LED. Each possibility is a separate embodiment. According to some embodiments, the light source is a tungsten halogen light source.

According to some embodiments, the one or more optical sensors comprise at least one hyperspectral camera.

According to some embodiments, the light source sensor is a temperature sensor, wherein the temperature sensor is selected from a thermal sensor, a thermocouple, a laser sensor, a thermistor or any combination thereof. Each possibility is a separate embodiment.

According to some embodiments, the light source sensor is a diode receptor configured to measure the intensity of the specific wavelength of the light emitted by the light source.

4

According to some embodiments, the light source sensor is a current and/or voltage monitor, such as but not limited to an AVOmeter.

According to some embodiments, the one or more optical sensors comprise at least one hyperspectral camera. Additionally or alternatively, the one or more optical sensors comprise at least one RGB camera.

According to some embodiments, the system further includes one or more additional sensors selected from a distance sensor, a lidar sensor, a depth sensor, a temperature sensor, an ultrasonic sensor, fluorescence sensor, X-ray sensor, XRF (X-ray fluorescence) sensor, MRI sensor, dielectric sensor, or any combination thereof. Each possibility is a separate embodiment.

According to some embodiments, the processing unit is configured to fuse the received spectral data with data received from additional sensors. According to some embodiments, the deriving of the internal and/or external quality attributes of the produce comprises feeding the fused data into a machine learning model.

According to some embodiments, the processing unit is further configured to produce a report presenting the derived internal and/or external quality attributes. According to some embodiments, the one or more internal and/or external parameters are selected from chemical composition, biochemical composition, physical composition and biophysical composition, like dry matter, total soluble solids, sugar content, moisture, acidity, titratable acidity, pH, starch, ascorbic acid, external and/or internal defects, moldiness, decay, pigments, size, shape, texture, contaminants, and any combination thereof. Each possibility is a separate embodiment.

According to some embodiments, the processing unit is further configured to derive one or more complex parameters from one or more of the internal and/or external quality attributes, wherein the one or more complex attribute comprise maturity, ripeness, shelf-life, storability and any combination thereof. Each possibility is a separate embodiment.

According to some embodiments, there is provided a system for determining external and/or internal attributes of an object, the system comprising:

a light source configured to illuminate an object;

a calibration board configured to reflect light having a known spectral profile, the known spectral profile indicative of a spectral emission profile of the light source;

an optical calibration board sensor configured to detect at least a portion of the light reflected by the calibration board;

one or more optical sensors operating in visual and/or non-visual spectra and configured to capture images of the illuminated object; and a processing unit configured to:

receive, as an input from the optical calibration board sensor, a signal indicative of the light reflected by the calibration board;

receive spectral data from the one or more optical sensors; and derive an internal and/or external quality attribute of the object based on the signal indicative of the light reflected by the calibration board and based on the received spectral data.

According to some embodiments, the light source is a halogen light source, a xenon light source or a LED. Each possibility is a separate embodiment. According to some embodiments, the light source is a tungsten halogen light source.

According to some embodiments, the one or more optical sensors comprise at least one hyperspectral camera. Additionally or alternatively, the one or more optical sensors comprise at least one RGB camera.

According to some embodiments, the light source sensor is a temperature sensor, wherein the temperature sensor is selected from a thermal sensor, a thermocouple, a laser sensor, a thermistor or any combination thereof. Each possibility is a separate embodiment.

According to some embodiments, the light source sensor is a diode receptor configured to measure the intensity of the specific wavelength of the light emitted by the light source.

According to some embodiments, the light source sensor is a current and/or voltage monitor.

According to some embodiments, the system further includes one or more additional sensors selected from a distance sensor, a lidar sensor, a depth sensor, a temperature sensor, an ultrasonic sensor, fluorescence sensor, X-ray sensor, XRF (X-ray fluorescence) sensor, MRI sensor, dielectric sensor, or any combination thereof. Each possibility is a separate embodiment.

According to some embodiments, the processing unit is configured to fuse the received spectral data with data received from additional sensors.

According to some embodiments, the deriving of the internal and/or external quality attributes of the produce comprises feeding the fused data into a machine learning model.

According to some embodiments, the processing unit is further configured to produce a report presenting the derived internal and/or external quality attributes. According to some embodiments, the one or more internal and/or external parameters are selected from chemical composition, biochemical composition, physical composition and biophysical composition, like dry matter, total soluble solids, sugar content, moisture, acidity, titratable acidity, pH, starch, ascorbic acid, external and/or internal defects, moldiness, decay, pigments, size, shape, texture, contaminants, and any combination thereof. Each possibility is a separate embodiment.

According to some embodiments, the processing unit is further configured to derive one or more complex parameters from one or more of the internal and/or external quality attributes, wherein the one or more complex attribute comprise maturity, ripeness, shelf-life, storability and any combination thereof. Each possibility is a separate embodiment.

According to some embodiments, the calibration board includes Polytetrafluoroethylene (PTFE).

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE FIGURES

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the disclosure. In block diagrams and flowcharts, certain steps may be conducted in the indicated order only, while others may be conducted before a previous step, after a subsequent step or simultaneously with another step. Such changes to the orders of the step will be evident for the skilled artisan/professional/craftsman.

FIG. 2 is an exemplary flow chart of a method for non-destructive, hyperspectral imaging based determining of external and/or internal attributes of an object, in particular external and/or internal attributes of a crop or crop load, according to some embodiments;

FIG. 4 is an exemplary flow chart of a method for non-destructive, hyperspectral imaging based determining of external and/or internal attributes of an object, in particular external and/or internal attributes of a crop or crop load, according to some embodiments;

FIG. 5 is an exemplary flow chart of a method for non-destructive, hyperspectral imaging based on the determination of external and/or internal attributes of an object, in particular external and/or internal attributes of a crop or crop load, according to some embodiments;

DETAILED DESCRIPTION

Figure 1:
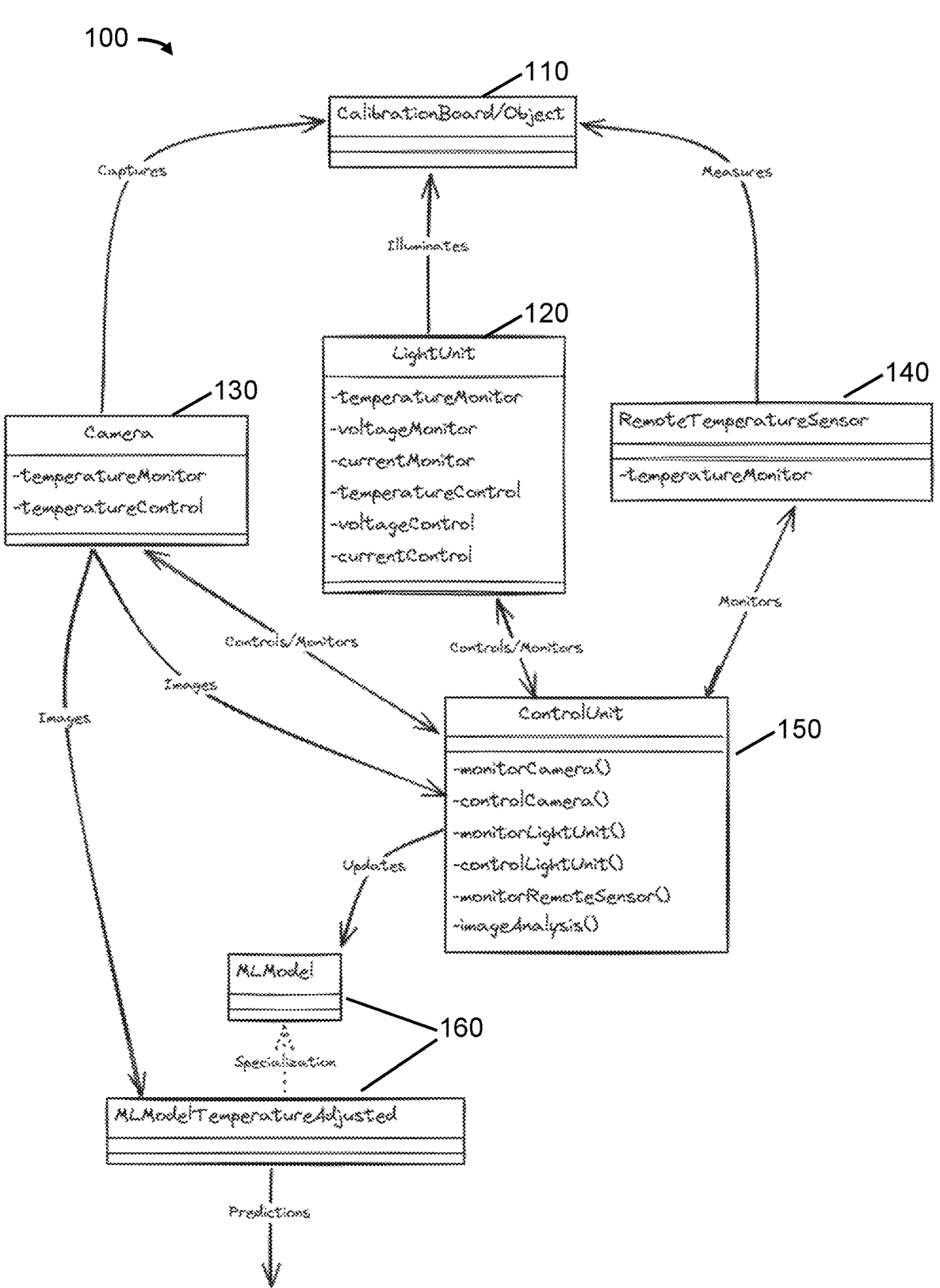
FIG. 1 is an operational flow chart of a system for non-destructive, hyperspectral imaging based determining of external and/or internal attributes of an object, in particular external and/or internal attributes of a crop or crop load, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided a system for non-destructive, real-time determination of external and/or internal attributes of an object, in particular the attributes of a produce or a produce load, based on hyperspectral imaging.

As used herein the term "hyperspectral imaging" refers to a process including collecting and processing information from across the electromagnetic spectrum to obtain the spectrum for each pixel in the image of a scene. That is, in hyperspectral imaging, the recorded spectra have fine wavelength resolution and cover a wide range of wavelengths. There are four ways for sensors to sample a hyperspectral cube, namely spatial scanning, spectral scanning, snapshot imaging, and spatio-spectral scanning.

As used herein, the term "produce" refers to a farm-produced crop, including fruits, vegetables, grains, oats, etc. More specifically, the term produce preferably refers to fresh products including post-harvest crop. According to some embodiments, the terms "crop" and "produce" may be used interchangeably.

As used herein, the term "produce load" refers to an aggregation of produce, such as at least 0.1 kg, at least 0.5 kg, at least 1 kg, at least 10 kg, at least 100 kg produce, at least 500 kg, at least 1000 kg, at least 5000 kg, or at least 10,000 kg. Each possibility is a separate embodiment. According to some embodiment, the produce load may be a crate, box, container, a truck load or the like.

As used herein, the terms "in real-time" and "on-the-fly", may be used interchangeably and refer to a produce evaluation which does not require destruction of the produce or lab test results. According to some embodiments, a real-time evaluation of an entire produce load may be completed in less than 1 hour, less than 30 min, less than 20 min, less than 15 minutes or less than 10 minutes or less than 5 minutes or less than 1 min.

According to some embodiments, at least one of the one or more light sources is a halogen light source, a xenon light source or a LED. According to some embodiments, at least one of the one or more light sources is a wavelength tunable light source, such as but not limited to a Zolix tunable light source.

As used herein, the terms "halogen light source", "halogen lamp" and "halogen light bulb" may be used interchangeably and refer to a light source that produces a wide spectrum of light, preferably from near ultraviolet to deep into the infrared spectrum. According to some embodiments, the halogen light source may be a continuous light source, i.e. include the entire spectrum. According to some embodiments, the halogen light source may be a non-continuous light source, including only portions of the entire spectrum or operating in a pulsating mode, such as but not limited to strobe light. According to some embodiments, all of the one or more light sources are halogen light sources.

As used herein, the terms "xenon light source", "xenon lamp" and "xenon light bulb" may be used interchangeably and refer to a type of gas discharge lamp, that produces a bright white light having a nearly continuous spectrum, when electricity a passed through the ionised xenon gas.

As used herein, the term "LED" may encompass continuous single LED illumination sources as well as an array of LEDs (e.g. 1, 2, 3, 4, 5 or more LEDs) collectively serving as a hyperspectral light source.

According to some embodiments, the light source may include more than one lamp. According to some embodiments, the light source may include 1, 2, 3, 4, 5, 6, 7, 8, 9, 10 or more light sources. Each possibility is a separate embodiment. According to some embodiments, the light sources may be spaced apart by a predetermined, optionally equal, distance from one another.

According to some embodiments, the power supply of the light source may be an AC or a DC power supply. According to some embodiments, the power supply, in particular for tungsten-halogen lamps, is a power supply that features a specialized circuitry that ensures current stabilization and suppressed ripple. The critical phase for a tungsten-halogen lamp is when voltage is first applied to a cold filament, a period when the filament resistance is approximately 20 times lower than it is at full operating temperature. Thus, when the supply voltage is instantaneously applied to the lamp by switching it on, a very high initial current flows (up to 10 times higher than steady state; termed inrush current) that slowly drops as the filament temperature and electrical resistance increase. Accordingly, utilizing the lamp typically requires initial time of warming and stabilizing the light source before acquiring appropriate images. Moreover, the high inrush current produced during a cold start unfortunately has a negative effect on the life expectancy of the lamp. The specialized power supply circuitry (often referred to as a soft start circuit) may advantageously be utilized to compensate for the high inrush currents in the most advanced applications (including microscopy) for which tungsten-halogen lamps are employed to conduct radiometric measurements. According to some embodiments, the power supply is an adjustable power supply that allows the output voltage and/or current to be programmed by a control circuit.

According to some embodiments, light signals obtained from the illuminated object may be detected by one or more optical sensors.

According to some embodiments, the one or more optical sensors comprise at least 2, at least 3, at least 4 or at least 5 optical sensors. Each possibility is a separate embodiment. According to some embodiments, the one or more optical sensors comprises a hyperspectral imaging camera/system.

According to some embodiments, the one or more optical sensors further comprise an RGB camera or hyperspectral imaging (HSI) camera. According to some embodiments, the one or more optical sensors further comprise a VIS-NIR or SWIR spectrophotometer or a HSI camera. According to some embodiments, the spectrophotometer/HSI camera has a spectral range of 350-1000 nm or 900-1700 nm or 300-2500 nm.

According to some embodiments, the spectral data detected by the one or more optical sensors may be inputted into a machine learning model trained to derive the internal and/or external quality attributes of the object based thereon.

However, as set forth above, the reliability of the hyperspectral imaging-based assessment of the object may be compromised due to changes in the spectral emission profile of the utilized light source.

Accordingly, according to some embodiments, the herein disclosed hyperspectral imaging system may include a light source sensor.

As used herein, the term "light source sensor" may refer to any sensor configured to directly or indirectly provide an indication regarding the spectral emission profile of the light source.

As used herein, the terms "spectral emission profile" and "emission spectrum" may be used interchangeably and refer to the spectrum of frequencies of electromagnetic radiation emitted due to electrons making a transition from a high energy state to a lower energy state. This collection of different transitions, leading to different radiated wavelengths, make up an emission spectrum.

According to some embodiments, the light source sensor may be a temperature sensor configured to directly or indirectly measure the temperature of the light source, which temperature in turn may be used to derive the spectral emission profile of the light source. Non-limiting examples of suitable temperature sensors include a thermal sensor, a thermocouple, a laser sensor, a thermistor or any combination thereof. Each possibility is a separate embodiment. Temperature sensors may be particularly suitable when the light source is a halogen lamp, which tends to heat during use.

According to some embodiments, the light source sensor may be a power dissipation sensor configured to measure the loss of electric potential energy (per unit time) in the form of heat by an electrical device when a current flows through it. The measured power dissipation may then be used to derive the spectral emission profile of the light source.

According to some embodiments, the power dissipation sensor may include a current and/or a voltage monitor. Power dissipation sensors may be particularly suitable for halogen lamps, which have a relatively high power dissipation.

According to some embodiments, the light source sensor may be a diode receptor configured to measure a specific wavelength of the light emitted by the light source. Since the wavelengths emitted by a halogen lamp get shorter with increasing temperature, an increase in the intensity of a short wavelength or a decrease in an intensity of long wavelength may be indicative of a change in the spectral emission profile of the light source, due to heating. Similarly changes in the intensity of a wavelength emitted by a light source may be indicative of a change in the spectral emission profile, for example due to extensive/prolonged use of the lamp.

According to some embodiments, a calibration board may be used in order to derive the spectral emission profile of the light source (in addition to or instead of the light source sensor). According to some embodiments, the calibration board may be characterized by having a surface which reflects light with a spectral profile that has a known dependence on the emission profile of the light source illuminating it. According to some embodiments, the calibration board is or includes White/Grey Teflon (Polytetrafluoroethylene (PTFE)), White/Grey Spectralon.

According to some embodiments, regardless of whether the temperature, the power dissipation or the intensity of a wavelength of the light source is measured, the herein disclosed system is advantageously configured to derive a spectral emission profile of the light source therefrom.

According to some embodiments, the derived spectral emission profile may be used to adjust the output voltage and/or current delivered to the light source by the power supply coupled thereto. According to some embodiments, the power supply is an adjustable power supply that allows the output voltage and/or current to be programmed by a control circuit. According to some embodiments, the control circuit may be programmed with a machine learning model configured to receive as an input the derived spectral emission profile of the light source (or sensor signals indicative thereof) and output an optimal output voltage and/or current, based thereon. According to some embodiments, the control circuit may be configured to automatically change the output voltage and/or current delivered to the light source according to the determined optimal output voltage and/or current. According to some embodiments, the energy power supply may include a programmable transformer.

Additionally or alternatively, the derived spectral emission profile may be used as an input to the above mentioned machine learning model trained to determine the external and/or internal attributes of objects. That is, in addition to the spectral data and optionally data from other sensors such as temperature sensors configured to measure the temperature of the object, the derived spectral emission profile may serve as an input to the algorithm. According to some embodiments, the ML model may, in addition to its training on the object related sensor data, be further trained on data obtained when imaging the objects with a light source(s) having changes in its (theirs) spectral emission profile, e.g. as a result of a temperature change. It is understood that according to some embodiments, it is the derived spectral emission profile that is inputted in the ML model, while according to other embodiments, the data inputted to the ML model may be the (raw) data measured by the light source sensor, or both.

Reference is now made to FIG. 1, which schematically illustrates, the herein disclosed system 100 for non-destructive, hyperspectral imaging based determination of external and/or internal attributes of an object, in particular external and/or internal attributes of a crop or crop load.

System 100 includes a stage 110 (or other suitable structure) configured to receive the object and allow imaging thereof. System 100 further includes a light unit 120 comprising one or more light sources configured to emit light on the object, optionally from various angles thereof; and a camera 130 (or other optical sensor) configured to capture images and/or light signals reflected by the object in response to being illuminated.

Preferable, system 100 further includes a temperature sensor 140 configured to directly or indirectly measure a temperature of the object. Optionally, system 100 further includes additional sensors (not shown) configured to measure additional parameters of the object. Non-limiting additional sensors include a distance sensor, a lidar sensor, a depth sensor, a temperature sensor, an ultrasonic sensor, fluorescence sensor, X-ray sensor, XRF (X-ray fluorescence) sensor, MRI sensor, dielectric sensor, or any combination thereof. Each possibility is a separate embodiment.

Advantageously, light unit 120 also includes a light source sensor, such as a temperature monitor, a voltage monitor (e.g. an AVOmeter), a current monitor or other suitable sensor (as further elaborated herein) configured to measure the temperature and/or power dissipation of the light source. According to some embodiments, light unit 120 includes a processing circuit configured to control the output voltage and/or current of the power supply powering the light source.

According to some embodiments, the data captured by/obtained from camera 130, light unit 120 and temperature sensor 140 is sent to a control unit 150 (which may be integral to or separate from light unit 120).

According to some embodiments, control unit 150 is configured to monitor and optionally control the operation of camera 130, light unit 120 and temperature sensor 140.

According to some embodiments, control unit 150 may be configured to control data acquisition by camera 130. According to some embodiments, control unit 150 may be configured to control one or more parameters of camera 130. According to some embodiments, the one or more parameters are selected from: a field of view, exposure time, aperture, gain, sensitivity, frame rate and any combination thereof. Each possibility is a separate embodiment. According to some embodiments, control unit 150 is configured to receive images of the object captured by camera 130. According to some embodiments, control unit 150 may be configured to adjust the one or more parameters of camera 130, based on the received images.

According to some embodiments, control unit 150 may be configured to control data acquisition by temperature sensor 140.

According to some embodiments, control unit 150 may be configured to control one or more parameters of light unit 120, such as but not limited to the position, orientation, light projection and/or light intensity of the light source. According to some embodiments, control unit 150 may be configured to receive data from the light source sensor of light unit 120. According to some embodiments, control unit 150 may be configured to adjust the one or more parameters of the one or more light sources of light unit 130, based on the data.

According to some embodiments, control unit 150 may be configured to control the output voltage and/or current delivered to the one or more light sources of light unit 120.

According to some embodiments, control unit 150 may be configured to derive a spectral emission profile of the one or more light sources of light unit 120, based on the data received from the light source sensor. According to some embodiments, control unit 150 may be configured to control the output voltage and/or current delivered to the one or more light sources of light unit 120, based on the derived spectral emission profile.

According to some embodiments, control unit 150 may include or be functionally connected to a processing circuitry 160 programmed to include an ML model trained to determine one or more external and/or internal attributes of the object, based at least on the images of the object received from camera 130 and or from control unit 150, and the temperature of the object as measured by temperature sensor 140, as well as optionally additional data received from any one or more additional sensors.

According to some embodiments, by controlling the output voltage and/or current supplied to the one or more light sources of light unit 120, the spectral emission profile of the light sources may be sufficiently constant in order to reliably assess the external and/or internal attributes of the object, based solely on the data received from camera 130, temperature sensor 140 and optionally additional sensors.

Additionally or alternatively, control unit 150 may be further configured to receive signals from the light source sensor of light unit 120, the signals indicative of the temperature of the one or more light sources and/or the power dissipation of the one or more light sources and/or the intensity of a particular wavelength emitted by the one or more light sources of light unit 120.

According to some embodiments, control unit 150 may then derive a spectral emission profile, based on the signals. According to some embodiments, control unit 150 may be further configured to input the signals(s) and/or the derived spectral emission profile to the ML model of processing circuitry 160, which may then determine the external and/or internal attributes of the object, based on the derived spectral emission profile of the one or more light sources or based on signals indicative thereof, in addition to the data received from camera 130, temperature sensor 140 and optionally additional sensors.

According to some embodiments, the one or more internal and/or external parameters are selected from chemical composition, biochemical composition, physical composition and biophysical composition, like dry matter, total soluble solids, sugar content, moisture, acidity, titratable acidity, pH, starch, ascorbic acid, external and/or internal defects, moldiness, decay, pigments, size, shape, texture, contaminants, and any combination thereof. Each possibility is a separate embodiment. According to some embodiments, the ML model may be further configured to derive one or more complex parameters from the one or more of the internal and/or external quality attributes, wherein the one or more complex attribute comprise maturity, ripeness, shelf-life, storability and any combination thereof. Each possibility is a separate embodiment.

According to some embodiments, prior to imaging the object, camara 130 may be configured to image a calibration surface position on stage 110. According to some embodiments, the calibration board is characterized by having a surface which reflects light with a spectral profile that has a known dependence on the emission profile of the one or more light sources of light unit 120 illuminating it.

According to some embodiments, the spectral data obtained when imaging the calibration board may be sent to control unit 150, which in turn may derive the spectral emission profile of the one or more light sources therefrom. According to some embodiments, the control unit 150 may then adjust the output voltage and/or current supplied to the one or more light sources, based on the calibration spectral data and/or the spectral emission profile derived therefrom. According to some embodiments, the control unit 150 may input the calibration spectral data and/or the spectral emission profile into the ML model of processing circuitry 160.

Reference is now made to FIG. 2, which is an illustrative flowchart of a method 200 for non-destructive, hyperspectral imaging based determining of external and/or internal attributes of an object, in particular external and/or internal attributes of a crop or crop load, according to some embodiments.

In step 210 an object (e.g. a produce) is positioned on a stage of a hyperspectral imaging chamber, which object in step 220 is illuminated by one or more light sources (e.g. by a tungsten halogen lamp), and in step 230 the temperature of the one or more light sources and/or the power dissipation of the one or more light sources and/or a wavelength intensity of the light emitted by the one or more light sources is measured by a light source sensor.

In step 240 a spectral emission profile may optionally be calculated, based on the data obtained from the light source sensor and, if required, the output voltage and/or current of the power supply of the one or more light sources may be adjusted, based on the calculated spectral emission profile or directly based on data received from the light source sensor, so as to maintain the spectral emission profile of the one or more light sources within a predetermined range. According to some embodiments, the adjustment of the voltage and/or current of the power supply may be controlled via a control circuit receiving the spectral emission profile and/or the data received from the light source sensor as an input (e.g. into an ML model thereof).

Once, the spectral emission profile of the one or more light sources is concluded to be within the predetermined range, images of the object may be captured (step 250) and its temperature measured.

An ML model may then be applied on the image and temperature data, which in turn outputs external and/or internal attributes of the object (step 260).

Figure 3:
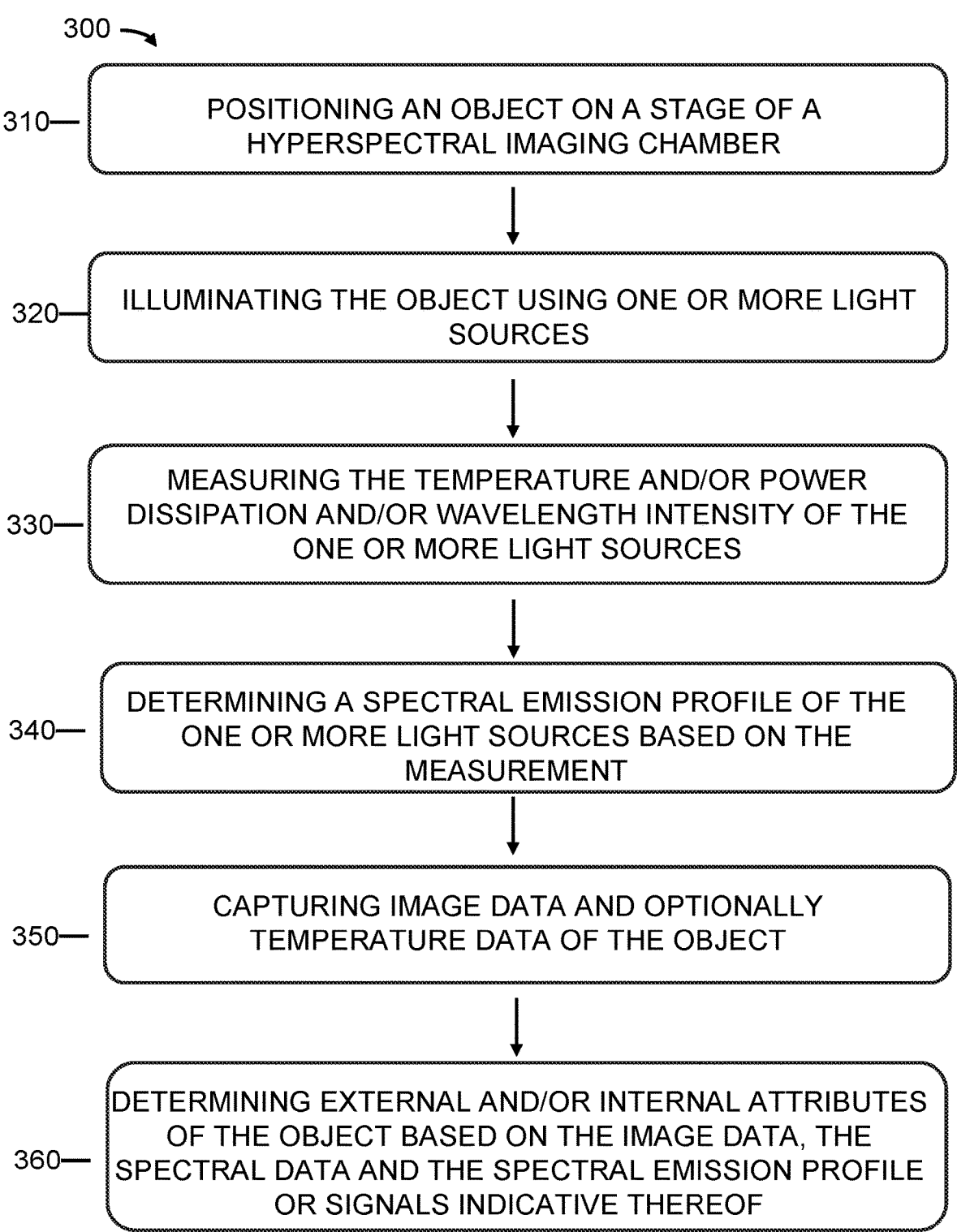
FIG. 3 is an exemplary flow chart of a method for non-destructive, hyperspectral imaging based determining of external and/or internal attributes of an object, in particular external and/or internal attributes of a crop or crop load, according to some embodiments.

Reference is now made to FIG. 3, which is an illustrative flowchart of a method 300 for non-destructive, hyperspectral imaging based determining of external and/or internal attributes of an object, in particular external and/or internal attributes of a crop or crop load, according to some embodiments.

In step 310 an object (e.g. a produce) is positioned on a stage of a hyperspectral imaging chamber, which object in step 320 is illuminated by one or more light sources (e.g. by a tungsten halogen lamp), and in step 330 the temperature of the one or more light sources and/or the power dissipation of the one or more light sources and/or a wavelength intensity of the light emitted by the one or more light sources is measured by a light source sensor.

In step 340 a spectral emission profile may optionally be calculated, based on the data obtained from the light source sensor.

Images of the object may then be captured (step 350) and its temperature measured.

An ML model may then be applied on the image and temperature data of the object, as well as on the spectral emission profile derived from the signals obtained from the one or more light sources, which ML model in turn outputs external and/or internal attributes of the object (step 360).

Reference is now made to FIG. 4, which is an illustrative flowchart of a method 400 for non-destructive, hyperspectral imaging based determining of external and/or internal attributes of an object, in particular external and/or internal attributes of a crop or crop load, according to some embodiments.

In step 410 a calibration board is positioned on a stage of a hyperspectral imaging chamber, which calibration board (in step 420) is illuminated by one or more light sources (e.g. by a tungsten halogen lamp).

In step 430 a spectral emission profile may optionally be determined, based on the light reflected by the calibration board. If required, the output voltage and/or current of the power supply of the one or more light sources may be adjusted, based on the calculated spectral emission profile or directly based on the detected light reflected from the calibration board, so as to maintain the spectral emission profile of the one or more light sources within a predetermined range (step 440). According to some embodiments, the adjustment of the voltage and/or current of the power supply may be controlled via a control circuit receiving the spectral emission profile, as an input (e.g. into an ML model thereof).

Once, the spectral emission profile of the one or more light sources is concluded to be within the predetermined range, an object (e.g. a produce) may be positioned on the stage (step 450), images thereof captured (step 460) and its temperature optionally measured.

An ML model may then be applied on the image and temperature data, which in turn outputs external and/or internal attributes of the object (step 260).

Reference is now made to FIG. 5, which is an illustrative flowchart of a method 500 for non-destructive, hyperspectral imaging based determining of external and/or internal attributes of an object, in particular external and/or internal attributes of a crop or crop load, according to some embodiments.

In step 510 a calibration board is positioned on a stage of a hyperspectral imaging chamber, and in step 520 the calibration board may be illuminated by one or more light sources (e.g. by a tungsten halogen lamp). In step 530 a spectral emission profile may optionally be determined, based on the light reflected by the calibration board.

The object (e.g. a produce) may then be positioned on the stage (step 540), images thereof captured (step 550) and its temperature measured.

An ML model may then be applied on the image and temperature data of the object, as well as on the spectral emission profile of the one or more light sources, which ML model in turn outputs external and/or internal attributes of the object (step 560).

Figure 6:
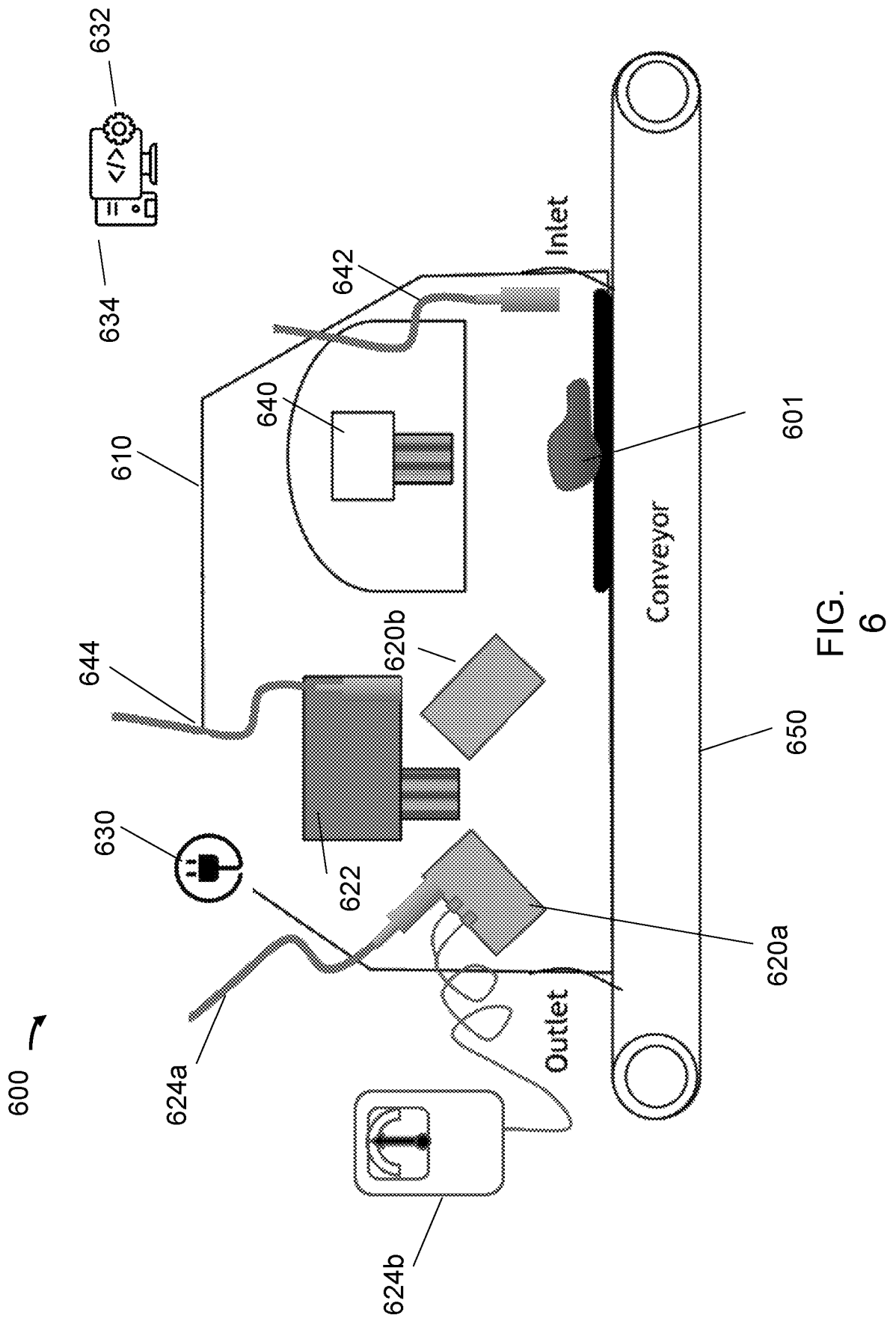
FIG. 6 is a schematic illustration of the setup of the herein disclosed system for non-destructive, hyperspectral imaging-based determination of external and/or internal attributes of an object.

Reference is now made to FIG. 6, which is a schematic illustration of the setup of the herein disclosed system 600 for non-destructive, hyperspectral imaging-based determination of external and/or internal attributes of an object, preferably a produce.

System 600 may optionally be a part of a production line and may be poisoned on/above a conveyer belt 650, to thereby facilitate real-time and in-line determination of the external and/or internal attributes of an object, here fruit 601.

System 600 includes a canopy 610 including a light sources 620a and 620b, here halogen lights configured to illuminate fruit 601 and a camera 622, here a hyper-spectral imager (HSI) can figured to capture light reflected from the illuminated fruit. System 600 further includes a light source sensor, such as a light source temperature sensor 624a and/or an AVOmeter 624b configured to directly and/or indirectly measure a temperature of light sources 620a and 620b and/or a power dissipation of light sources 620a and 620b and/or an intensity of a specific wavelength of the light emitted by light source 620a and 620b.

System 600 further includes a power supply 630 configured to supply power to light sources 620a and 620b and a control unit 632 configured to adjust a frequency, a current, and/or a voltage of power supply 630, based on the temperature and/or power dissipation and/or the intensity of the specific wavelength of light sources 620a and 620b measured by light source temperature sensor 624a and/or AVOmeter 624b, thereby ensuring that the spectral emission profile of light sources 620a and 620b is maintained within a predetermined range.

System 600 further includes one or more optical sensors operating in visual and/or non-visual spectra and configured to capture images of the illuminated object. Here, the optical sensor is a RGB camera 640.

Optionally, system 600 may further include additional sensors, here a temperature sensor 642 configured to measure the temperature of the object.

As a further option, system 600 may further include a temperature sensor 644 configured to measure the temperature of camera 622, to ensure proper function and maintenance thereof.

In addition, system 600 further includes a processing unit 634, here shown to be closely associated with control unit 632 however, processor may also be a remote stand-alone unit. Processing unit 634 is configured to receive spectral data from camera 622 and from the one or more optical sensors (here illustrated as RGB camera) and optionally also from temperature sensor 642 and to derive an internal and/or external quality attribute of the object, based on the received data.

The following examples are presented in order to more fully illustrate some embodiments of the invention. They should in no way be construed, however, as limiting the broad scope of the invention. One skilled in the art can readily devise many variations and modifications of the principles disclosed herein without departing from the scope of the invention.

Although some embodiments of the invention are not limited in this regard, discussions utilizing terms such as, for example, "processing", "computing", "calculating", "determining", "establishing", "analysing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

As used herein, the terms "approximately", "essentially" and "about" in reference to a number are generally taken to include numbers that fall within a range of 5% or in the range of 1% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

As used herein, the singular forms "a," "an" and "the" include plural referents unless the context clearly dictates otherwise.

As used herein, "optional" or "optionally" means that the subsequently described event or circumstance does or does not occur, and that the description includes instances where said event or circumstance occurs and instances where it does not.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although stages of methods, according to some embodiments, may be described in a specific sequence, the methods of the disclosure may include some or all of the described stages carried out in a different order. In particular, it is to be understood that the order of stages and substages of any of the described methods may be reordered unless the context clearly dictates otherwise, for example, when a latter stage requires as input an output of a former stage or when a latter stage requires a product of a former stage. A method of the disclosure may include a few of the stages described or all of the stages described. No particular stage in a disclosed method is to be considered an essential stage of that method, unless explicitly specified as such.

Although the disclosure is described in conjunction with specific embodiments thereof, it is evident that numerous alternatives, modifications, and variations that are apparent to those skilled in the art may exist. Accordingly, the disclosure embraces all such alternatives, modifications, and variations that fall within the scope of the appended claims. It is to be understood that the disclosure is not necessarily limited in its application to the details of construction and the arrangement of the components and/or methods set forth herein. Other embodiments may be practiced, and an embodiment may be carried out in various ways.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A system for determining external and/or internal attributes of a produce, the system comprising:
   a halogen light source configured to illuminate the produce;
   a light source sensor configured to generate a signal indicative of a spectral emission profile of the halogen light source, wherein the light source sensor is a temperature sensor or a current and/or voltage monitor;
   a power supply coupled to the halogen light source and configured to supply power to the halogen light source;
   a control unit capable of adjusting a frequency, a current, and/or a voltage of the power supply;
   one or more optical sensors operating in visual and/or non-visual spectra and configured to capture images of the illuminated produce; and
   a processing unit configured to:
      receive the signal from the light source sensor and to compute a spectral emission profile of the halogen light source, based thereon;
      dynamically trigger the control unit to adjust a frequency, a current, and/or a voltage of the power supply, based on the computed spectral emission profile, so as to maintain the spectral emission profile of the halogen light source within a predetermined range;
      receive spectral data from the one or more optical sensors after adjustment of the power supply; and
      derive an internal and/or external quality attribute of the produce, based on the spectral data, based on the spectral data received from the one or more optical sensors.

2. The system of claim 1, wherein the temperature sensor is selected from a thermal sensor, a thermocouple, a thermistor or any combination thereof.

3. The system of claim 1, further comprising a diode receptor configured to measure the intensity of the specific wavelength of the light emitted by the light source.

4. The system of claim 1, further comprising one or more additional sensors configured to measure one or more parameters of the illuminated produce; the additional sensor selected from a distance sensor, a lidar sensor, a depth sensor, a temperature sensor, an ultrasonic sensor, fluorescence sensor, X-ray sensor, XRF (X-ray fluorescence) sensor, MRI sensor, dielectric sensor, or any combination thereof.

5. The system of claim 1, wherein the one or more optical sensors comprise at least one hyperspectral camera.

6. A system for determining external and/or internal attributes of a produce, the system comprising:
   a halogen light source configured to illuminate the produce;
   a light source sensor configured to generate a signal indicative of a spectral emission profile of the halogen light source, wherein the light source sensor is a temperature sensor or a current and/or voltage monitor;
   one or more optical sensors operating in visual and/or non-visual spectra and configured to capture images of the illuminated produce; and
   a processing unit programmed with a machine learning model configured to:
      receive as an input the sensor signals or the spectral emission profile derived therefrom and output an optimal output voltage and/or current, based thereon:
      receive spectral data from the one or more optical sensors; and
      output an internal and/or external quality attribute of the produce based on the received sensor signals or the spectral emission profile derived therefrom and the received spectral data.

7. The system of claim 6, wherein the one or more optical sensors comprise at least one hyperspectral camera.

8. The system of claim 6, wherein the temperature sensor is selected from a thermal sensor, a thermocouple, a thermistor or any combination thereof.

9. The system of claim 6, further comprising a diode receptor configured to measure the intensity of the specific wavelength of the light emitted by the light source.

* * * * *